Figure 1:
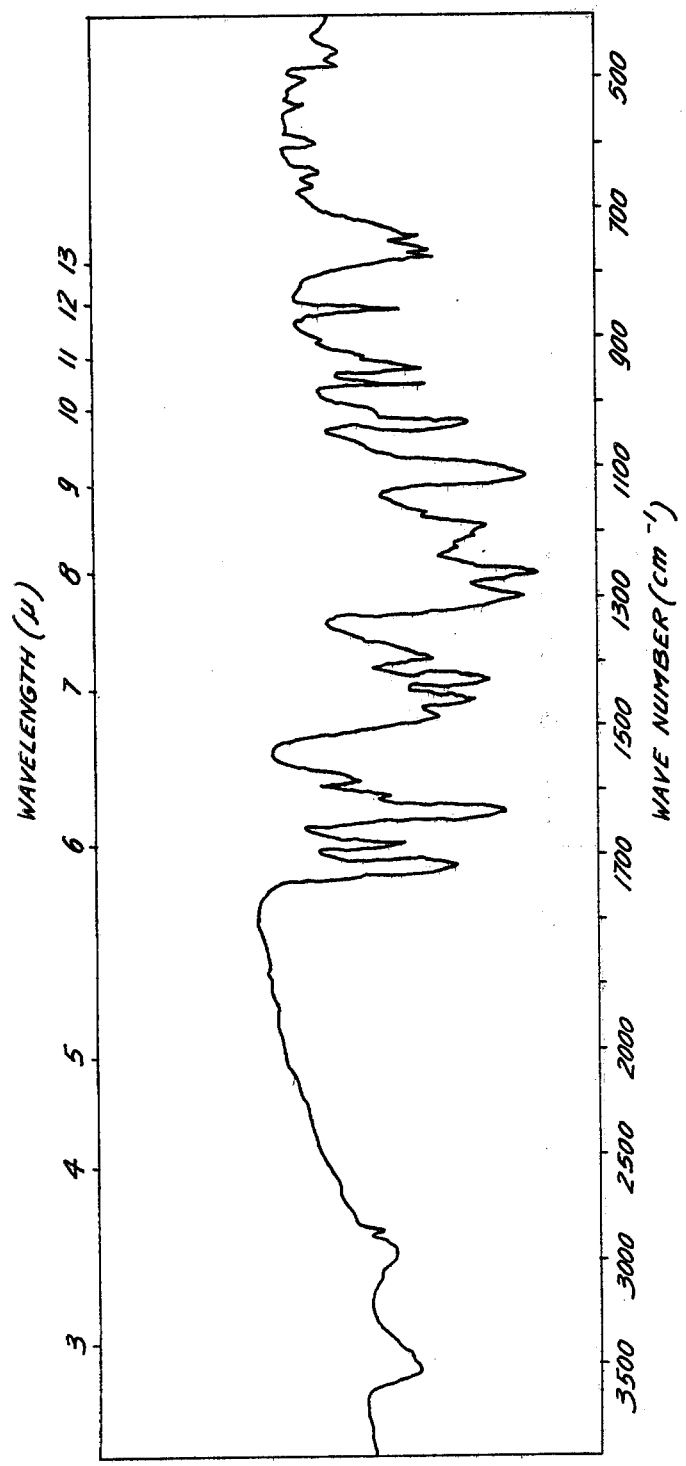

United States Patent [19]

Fujiwara et al.

[11] 4,304,861
[45] Dec. 8, 1981

[54] **PROCESS OF PRODUCING ANTIBIOTIC SM-173B WITH *STREPTOMYCES CHROMOFUSCUS***

[75] Inventors: Akiko Fujiwara; Mitsuhiko Fujiwara, both of Kamakura; Tatsuo Hoshino, Fujisawa; Yuzuru Sekine, Yokohama; Masaaki Tazoe, Fujisawa, all of Japan

[73] Assignee: Hoffmann-La Roche Inc., Nutley, N.J.

[21] Appl. No.: 92,402

[22] Filed: Nov. 8, 1979

Related U.S. Application Data

[62] Division of Ser. No. 875,050, Feb. 3, 1978, Pat. No. 4,206,169.

[30] Foreign Application Priority Data

Feb. 4, 1977 [AT] Austria ................................. 747/77

[51] Int. Cl.³ .............................................. C12P 15/00
[52] U.S. Cl. ..................................... 435/127; 435/886
[58] Field of Search ................................ 435/127, 886

[56] References Cited

U.S. PATENT DOCUMENTS 4,194,064  3/1980  Omura et al. .................... 435/127 X

*Primary Examiner*—Lionel M. Shapiro
*Attorney, Agent, or Firm*—Jon S. Saxe; Bernard S. Leon; Frank P. Hoffman

[57] ABSTRACT

A novel antibiotic having the ascribed formula

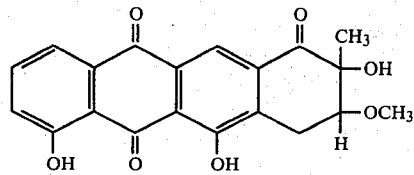

is provided. They physical characteristics are as follows:

(a) Elementary analysis: Calculated (for $C_{20}H_{16}O_7$): C,65.22; H,4.35%. Found: C,64.60; H,4.34%.
(b) Molecular weight (mass-spectrometric): 368.
(c) Melting point: 225°–226° C.
(d) Specific rotation: $[\alpha]_D^{20} = +123.5°$ (c=0.2 in chloroform).
(e) Ultraviolet absorption spectrum:
$\lambda_{max}^{methanol} = 235$ nm ($\epsilon=28600$); 262 nm ($\epsilon=21900$); 434–435 nm ($\epsilon=11300$);
$\lambda_{max}^{0.1-N\ NaOH/methanol} = 246$ nm ($\epsilon=22400$); 256 nm ($\epsilon=23200$); 523–524 nm ($\epsilon=9600$).
(f) Infrared absorption spectrum: 3500, 1710, 1672, 1628, 1600, 1575, 1472, 1452, 1420, 1390, 1295, 1255, 1218, 1200, 1182, 1105, 1025, 1005, 962, 938, 848, 765, 752, 730 cm$^{-1}$.
(g) Solubility: Soluble in methanol, ethanol, butanol, acetone, chloroform, ethyl acetate and in water under alkaline conditions; poorly soluble in n-hexane; insoluble in petroleum ether and water.
(h) Color reactions: Positive with sulfuric acid and iodine; negative with ninhydrin and anisaldehyde.
(i) NMR spectrum in DC.Cl₃: 1.42 ppm (3H, singlet), 3.02 ppm (1H, quartet), 3.43 ppm (3H, singlet), 3.62 ppm (1H, triplet), 3.64 ppm (1H, singlet), 3.93 ppm (1H, triplet), 7.31–3.41 ppm (4H, olefinic protons), 12.0 ppm (1H, singlet), 12.5 ppm (1H, singlet).

Also provided is a process for the antibiotic's production.

1 Claim, 2 Drawing Figures

PROCESS OF PRODUCING ANTIBIOTIC SM-173B WITH *STREPTOMYCES CHROMOFUSCUS*

This is a division of application Ser. No. 875,050 filed Feb. 3, 1978, now U.S. Pat. No. 4,206,169, issued July 3, 1980.

DESCRIPTION OF THE INVENTION

The present invention relates to a novel antibiotic. More particularly, the invention is concerned with a novel antibiotic, referred to hereinafter as antibiotic SM-173B, a process for the manufacture thereof and pharmaceutical preparations containing same.

The novel antibiotic SM-173B provided by the present invention is an orange-coloured, weakly acid substance and has the following physico-chemical properties:

(a) Elementary analysis: Calculated (for $C_{20}H_{16}O_7$): C, 65.22; H, 4.35%. Found: C, 64.60; H, 4.34%.

(b) Molecular weight (mass-spectrometric): 368.

(c) Melting point: 225°–226° C.

(d) Specific rotation: $[\alpha]_D^{20} = +123.5°$ (c=0.2 in chloroform).

(e) Ultraviolet absorption spectrum:
$\lambda_{max}^{methanol} = 235$ nm ($\epsilon = 28600$); 262 nm ($\epsilon = 21900$); 434–435 nm ($\epsilon = 11300$);
$\lambda_{max}^{0.1\text{-}N\ NaOH/methanol} = 246$ nm ($\epsilon = 22400$); 256 nm ($\epsilon = 23200$); 523–524 nm ($\epsilon = 9600$).

(f) Infrared absorption spectrum (FIG. 1) 3500, 1710, 1672, 1628, 1600, 1575, 1472, 1452, 1420, 1390, 1295, 1255, 1218, 1200, 1182, 1105, 1025, 1005, 962, 938, 848, 765, 752, 730 cm$^{-1}$.

(g) Solubility: Soluble in methanol, ethanol, butanol, acetone, chloroform, ethyl acetate and in water under alkaline conditions; poorly soluble in n-hexane; insoluble in petroleum ether and water.

(h) Colour reactions: Positive with sulfuric acid and iodine; negative with ninhydrin and anisaldehyde.

Figure 2:
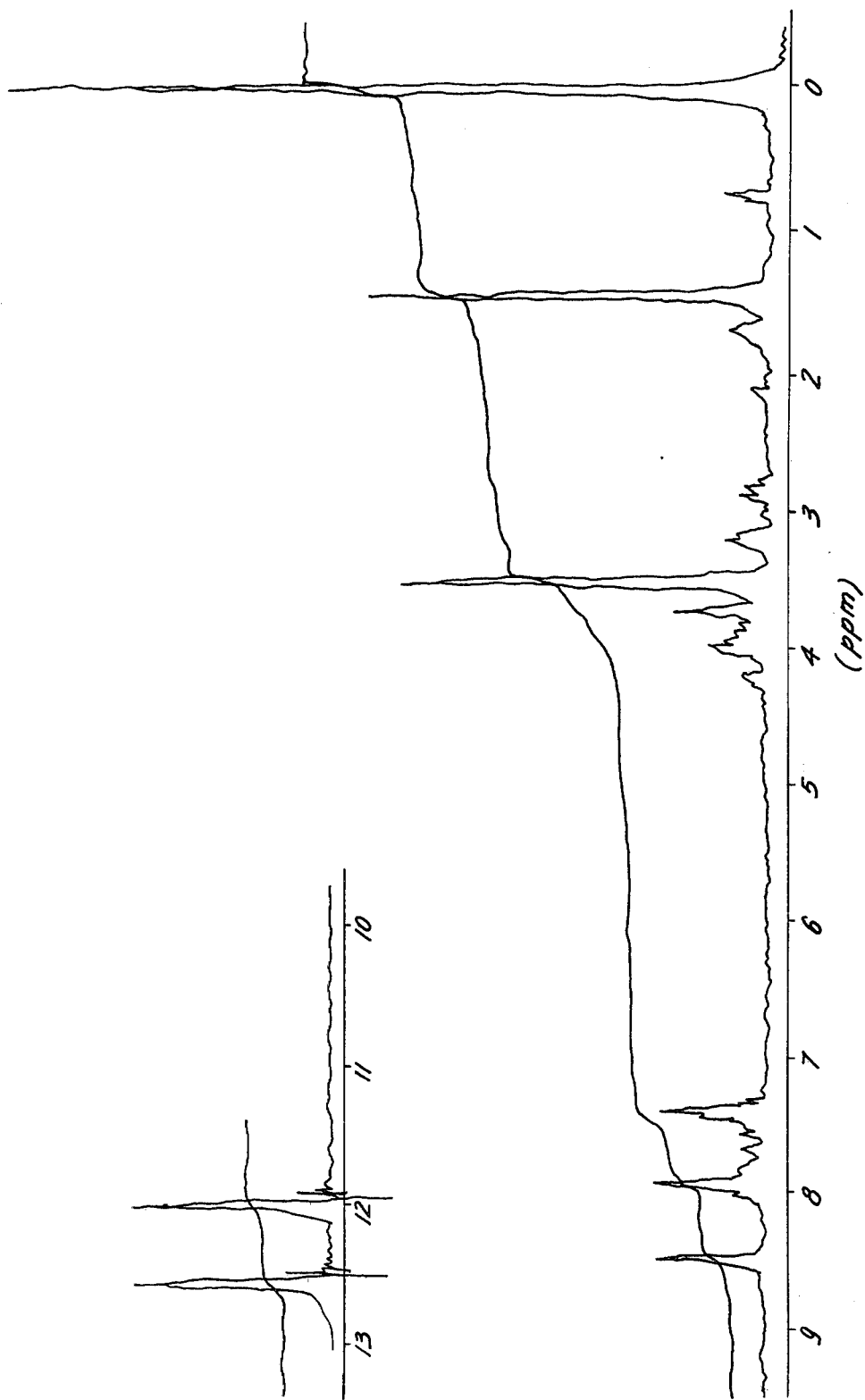

(i) NMR spectrum in DC.Cl$_3$ (FIG. 2) 1.42 ppm (3H, singlet), 3.02 ppm (1H, quartet), 3.43 ppm (3H, singlet), 3.62 ppm (1H, triplet), 3.64 ppm (1H, singlet) 3.93 ppm (1H, triplet), 7.31–8.41 ppm (4H, olefinic protons), 12.0 ppm (1H, singlet), 12.5 ppm (1H, singlet).

Antibiotic SM-173B provided by the present invention is a compound of the anthracylinone series. Antibiotic SM-173B differs, however, in its physico-chemical properties from the hitherto known antibiotics of this series and accordingly represents a novel substance to which can be ascribed the following formula

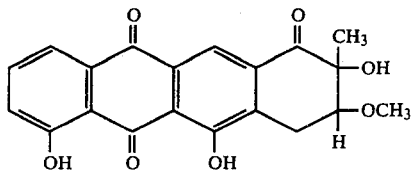

The biological properties of antibiotic SM-173B provided by the present invention are as follows:

1. Antibacterial properties

The antibacterial spectrum is evident from the following Table:

| Minimum Inhibitory Concentration (MIC) | |
|---|---|
| Test organism | MIC (µg/ml) |
| *Staphylococcus aureus* 209P | 6.25 |
| *Staphylococcus epidermidis* | 3.13 |
| *Sarcina lutea* | 12.5 |
| *Bacillus subtilis* | 6.25 |
| *Bacillus cereus* | 6.26 |
| *Micrococcus flavus* | 6.25 |
| *Echerichia coli* | 100 |
| *Mycobacterium avium* | 6.25 |
| *Mycobacterium smegmatis* | 3.13 |
| *Mycobacterium rhodochrous* | 3.13 |
| *Aspergillus niger* | 100 |
| *Penicillium citrinum* | 100 |

2. Toxicity

The LD$_{50}$ is greater than 200 mg/kg in the case of intraperitoneal administration to mice.

As can be seen from the above Table, antibiotic SM-173B is antibiotically active against a large number of gram-positive bacteria and against mycobacteria. It can accordingly be used as a disinfection agent and also as a therapeutic agent. When used as a therapeutic agent, the dosage will depend upon the individual requirements of the patient and the directions of the attending physician. In general, daily dosages of about 200 mg to 1000 mg are administered orally or parenterally to adults; the lower dosages being applicable in the case of parenteral administration.

The antibiotic SM-173B provided by the present invention can be used, for example, in the form of pharmaceutical preparations which contain it in association with a compatible pharmaceutical carrier material. This carrier material can be an organic or inorganic inert carrier material which is suitable for enteral, percutaneous or parenteral administration such as, for example, water, gelatin, gum arabic, lactose, starch, magnesium stearate, talc, vegetable oils, polyalkyleneglycols, petroleum jelly etc. The pharmaceutical preparations can be made up in solid form (e.g. as tablets, dragees, suppositories or capsules), in a semisolid form (e.g. as salves) or in a liquid (e.g. as solutions, suspensions or emulsions). The pharmaceutical preparations may be sterilized and/or may contain adjuvants such as preserving, stabilizing, wetting or emulsifying agents, salts for varying the osmotic pressure or substances acting as buffers. The pharmaceutical preparations can contain other therapeutically valuable substances.

According to the process provided by the present invention, antibiotic SM-173B is manufactured by cultivating an antibiotic SM-173B-producing microorganism of the genus Streptomyces under aerobic conditions in an aqueous culture medium and isolating antibiotic SM-173B from the fermentation broth.

The microorganism used in the foregoing process can be any strain (including variants) of the genus Streptomyces which is capable of producing antibiotic SM-173B. Preferred strains are *Streptomyces chromofuscus* SM-173 as well as variants thereof. *Streptomyces chromofuscus* SM-173 was isolated from soil from Kumamoto-ken, Japan, and identified as a strain belonging to *Streptomyces chromofuscus*.

The strain denoted as *Streptomyces chromofuscus* SM-173 has been deposited with the Fermentation Research Institute, Agency of Industrial Science and Technology, Japan, under the number "FERM-P No. 3824". A subculture of this deposited strain has been deposited in the microorganism collection of the U.S. Department of Agriculture, Northern Utilization Research and Development Division, Peoria, Ill., U.S.A., under No. NRRL 11092. The mycological features of the Streptomyces deposited as FERM-P No. 3824 and NRRL 11092 are as follows:

I. Morphology: Aerial mycelium forms abundantly on oatmeal agar, inorganic salts/starch agar and Bennet's agar; the spore formation is abundant. The mycelium branches irregularly and each branch terminates in predominantly opened spirals having more than 5 turns. Ripe spore chains having more than 10 spores per chain are generally formed. The surface structure of the spore is spiny upon observation under an electron microscope.

II. Culture characteristics:
   Yeast/malt agar: Abundant growth, aerial mycelium grey, reverse yellowish-brown to yellowish-orange, no formation of soluble pigment.
   Oatmeal agar: Good growth, aerial mycelium grey, reverse yellowish-brown to yellowish-orange, no formation of soluble pigment.
   Salt/starch agar, glycerine/asparagine agar: As yeast/malt agar.
   Nutrient agar: Moderate growth, little aerial mycelium, reverse brown to dark brown, no formation of soluble pigment.
   Sucrose/nitrate agar: Weak growth.

III. Physiological properties:
   (i) Temperature range on Bennet's agar: Abundant growth and spore formation at 26° C., 30° C. and 37° C.
   (ii) Gelatine liquefaction: Negative (20° C.; 7 days on glucose/peptone/gelatine medium).
   (iii) Starch hydrolysis: Negative
   (iv) Action on milk (10% skimmed milk): Coagulation negative. Peptonisation weakly positive.
   (v) Melanin pigment formation: Peptone/yeast/iron agar positive. Tryptone/yeast broth positive. Tyrosine agar negative.

IV. Utilization of carbon sources (on Pridham-Gottlieb's agar):
   All of the carbon sources named hereinafter are used positively: L-arabinose, D-glucose, D-fructose, D-xylose, D-mannitol, inositol, rhamnose, raffinose, sucrose.

The aforementioned characteristics of the strain SM-173 can be summarized as follows: The aerial mycelium consists of opened spirals and the surface structure of the spores is spiny. The aerial mycelium is grey. Malanin-like pigments are formed on peptone/yeast/iron agar, but not on tyrosine agar. The formation of other soluble pigments is rarely observed.

In the investigation of strains standing in close relationship to the strain SM-173, it was found, with reference to the publications of the "International Streptomyces Projects" (ISP) in the "International Journal of Systematic Bacteriology", Vol. 18, pages 69–189, 279–392 (1968), Vol. 19, pages 391–512 (1969) and Vol. 22, pages 265–394 (1972), that the strain SM-173 very closely resembled the strain *Streptomyces chromofuscus*. Both strains are identical in morphological features, the formation of spirals and spiny spores, the formation of grey aerial mycelium and of melanin-like pigment on peptone/yeast/iron agar, but not on tyrosine agar. Detailed comparison of the two strains shows that the type-strain *Streptomyces chromofuscus* does not utilize sucrose, whereas the strain SM-173 does utilize sucrose. Moreover, the strain SM-173 forms much better spores than the type-culture. These differences can, however, hardly be sufficient to create a new variety or species.

It is evident that there is a close relationship between strain SM-173 and the type-strain *Streptomyces chromofuscus*. Based on these observations, the strain SM-173 was designated as *Streptomyces chromofuscus* SM-173 and deposited as indicated earlier.

The cultivation in accordance with the process provided by the present invention can be carried out in a culture medium which contains customary nutrients usable by the microorganism being cultivated. As carbon sources there can be mentioned, for example, glucose, sucrose, starch, glycerine, molasses, dextrin and mixtures thereof. Nitrogen sources are, for example, soyabean meal, cottonseed meal, meat extract, peptone, dried yeast cornsteep liquor, ammonium sulphate, sodium nitrate and mixtures thereof. Moreover, there may be added to the culture medium other organic or inorganic substances for promoting the growth of the microorganism and for increasing the production of antibiotic SM-173B, examples of such substances being inorganic salts such as, for example, calcium carbonate, sodium chloride, phosphates and the like.

The cultivation is carried out under aerobic conditions in an aqueous medium, preferably by submerged fermentation. The cultivation is suitably carried out at a temperature of 25°–35° C., the optimal temperature being 28° C. The cultivation is preferably carried out at a pH of 5 to 8. The cultivation time depends on the conditions under which the cultivation is carried out. In general, it is sufficient to carry out the cultivation for 20–100 hours.

The isolation of antibiotic SM-173B from the fermentation broth can be carried out according to methods known per se. For example, the mycelium can be separated from the fermentation broth by centrifugation or filtration and antibiotic SM-173B can be extracted from the filtrate with a water-immiscible organic solvent such as ethyl acetate, butyl acetate etc. On the other hand, antibiotic SM-173B contained in the separated mycelium can be obtained, for example, by extracting the mycelium with a solvent such as aqueous acetone or aqueous methanol, removing the solvent and further extracting the residue with a water-immiscible organic solvent. The thus-obtained solvent phase is dried with a dehydrating agent such as sodium sulphate etc and then concentrated under reduced pressure. The resulting crude antibiotic SM-173B can be purified by means of extraction methods, precipitation methods, column-chromatographical methods (using silica gel, aluminium oxide etc as adsorbants) or by means of molecular sieve methods.

The following Example illustrates the process provided by the present invention:

EXAMPLE 1

Spores of *Streptomyces chromofurcus* SM-173 (deposited under No. 3824 with the Fermentation Research Institute, Agency of Industrial Science and Technology, Chiba, Japan, as well as under No. 11092 in the microorganism collection of the U.S. Department of Agriculture, Northern Utilization Research and Development Division, Peoria, Ill., U.S.A.) were inoculated into six 500 ml flasks each containing 100 ml of nutrient medium [2% glucose, 1% Pharmamedia (cottonseed oil, Traders Oil Mill, Texas, U.S.A.), 0.5% yeast powder (Ebios Pharmaceutical Co. Ltd., Japan), 1% wheat gluten] and cultivated at 28° C. for 3 days while shaking. The culture broth was used to inoculate 30 liters of nutrient medium having the same composition in a 50 liter fermenter. The cultivation was carried out at 27° C. while stirring (500 revolutions per minute) and aerating (30 liters per minute). After 48 hours, the culture was centrifuged, there being obtained 22 liters of filtrate. The filtrate was extracted twice with the same volume of ethyl acetate. The extracts were dried over sodium sulphate and concentrated in vacuo. There were thus obtained 12 ml of crude antibiotic SM-173B in the form of a yellow syrup. This syrup was added to a silica gel column (diameter 4 cm, height 60 cm, Kieselgel 60, Merck) and antibiotic SM-173B was eluted with chloroform. The fractions which contained only antibiotic SM-173B [determined with thin-layer chromatography plates, silica gel, benzene/acetone (4:3)] were combined and concentrated to 10 ml under reduced pressure. A small amount of n-hexane was added to the concentration which was then stored in the cold overnight. There was thus obtained antibiotic SM-173B in the form of orange-coloured crystals.

On the other hand, the mycelium obtained and collected in the process described earlier was extracted with 15 liters of acetone. After separating the mycelium cake and the solvent, the extract was extracted twice with 3.5 liters of ethyl acetate each time and dried over sodium sulphate. After concentration under reduced pressure, there was obtained crude antibiotic SM-173B in the form of a syrup. This syrup was absorbed on silica gel (silicic acid, Mallincrodt) in a glass column (diameter 4 cm, height 50 cm). Antibiotic SM-173B was eluted from the column with a mixture of benzene and acetone (95:5). The fractions which contained only antibiotic SM-173B (determined as described in the preceding paragraph) were pooled and evaporated to dryness in vacuo. The concentrate was dissolved in a small amount of hot benzene and left to stand overnight. There was thus obtained further antibiotic SM-173B in the form of orange-coloured crystals.

The following Example illustrates a typical pharmaceutical preparation containing antibiotic SM-173B:

EXAMPLE A

Tablets containing the following ingredients are produced:

| Ingredient | per tablet |
| --- | --- |
| Antibiotic SM-173B | 1.0 mg |
| Anhydrous lactose | 137.0 mg |
| Maize starch | 20.0 mg |
| Microcrystalline cellulose | 40.0 mg |
| Magnesium stearate | 2.0 mg |
| | 200.0 mg |

The active ingredient (antibiotic SM-173B) is mixed with a portion of the anhydrous lactose to form a premix. This premix is milled and then mixed for 15 minutes with the maize starch, the remaining anhydrous lactose and the microcrystalline cellulose. The resulting mixture is milled and subsequently mixed for 2 minutes with the magnesium stearate. The mixture obtained is pressed to tablets weighing 200 mg and having a diameter of 6 mm. The tablets can be flat or biconvex and can be provided with a break-bar if desired.

What is claimed:

1. A process for the manufacture of the novel antibiotic SM-173B, having the following physical characteristics:
   (a) elementary analysis: Calculated (for $C_{20}H_{16}O_7$): C, 65.22; H, 4.35%; Found: C, 64.60; H, 4.34%;
   (b) molecular weight (mass-spectrometric): 368
   (c) melting point: 225°–226° C.
   (d) specific rotation: $\alpha_D^{20} = +123.5°$ (c=0.2 in chloroform)
   (e) ultraviolet absorption spectrum:
   $\lambda_{max}^{methanol} = 235$ nm ($\epsilon=28600$); 262 nm ($\epsilon=21900$); 434–435 nm ($\epsilon=11300$);
   $\lambda_{max}^{0.1-N\ NaOH/methanol} = 246$ nm ($\epsilon=22400$); 256 nm ($\epsilon=23200$); 523–524 nm ($\epsilon=9600$);
   (f) infrared absorption spectrum (FIG. 1) 3500, 1710, 1672, 1628, 1600, 1575, 1472, 1452, 1420, 1390, 1295, 1255, 1218, 1200, 1182, 1105, 1025, 1005, 962, 938, 843, 765, 752, 730 cm$^{-1}$
   (g) solubility: soluble in methanol, ethanol, butanol, acetone, chloroform, ethyl acetate and in water under alkaline conditions; poorly soluble in n-hexane; insoluble in petroleum ether and water
   (h) color reactions: positive with sulfuric acid and iodine; negative with ninhydrin and anisaldehyde
   which process comprises cultivating an antibiotic SM-173B-producing microorganism of the genus *Streptomyces chromofuscus* under aerobic conditions in an aqueous culture medium and isolating antibiotic SM-173B from the fermentation broth.

* * * * *